United States Patent [19]
Johnson

[11] Patent Number: 4,971,071
[45] Date of Patent: Nov. 20, 1990

[54] CONDUCTIVE CONDOM

[75] Inventor: Gary D. Johnson, New York, N.Y.

[73] Assignees: Stanley Hochfeld, Howard Beach; Leonard Holtz, Oceanside, both of N.Y.

[21] Appl. No.: 381,135

[22] Filed: Jul. 14, 1989

[51] Int. Cl.[5] .......................... A61F 6/02; A61F 6/04; A61F 5/00; A61F 5/44
[52] U.S. Cl. .................................... 128/842; 128/844; 128/79; 604/347
[58] Field of Search .......................... 128/842, 844, 79; 604/347-353, 330; 252/500, 501, 511

[56] References Cited

U.S. PATENT DOCUMENTS

| | | | |
|---|---|---|---|
| 749,382 | 1/1904 | Henderson | 604/350 |
| 2,591,783 | 4/1952 | Craddock | 604/353 |
| 2,610,630 | 9/1952 | Crew | 604/347 |
| 3,405,714 | 10/1968 | Moss | 604/350 |
| 3,809,090 | 5/1974 | Poulacs | 604/347 |
| 4,354,494 | 10/1982 | Hogin | 128/79 |
| 4,381,000 | 4/1983 | Duncan | 128/79 |
| 4,415,548 | 11/1983 | Reddy | 128/844 |
| 4,678,601 | 7/1987 | Hem | 252/500 |
| 4,765,930 | 8/1988 | Mashimo | 252/511 |
| 4,781,709 | 11/1988 | Grubman | 604/349 |
| 4,840,624 | 6/1989 | Lee | 604/353 |

FOREIGN PATENT DOCUMENTS

| | | | |
|---|---|---|---|
| 0050257 | 6/1911 | Australia | 604/349 |
| 0267218 | 11/1913 | Fed. Rep. of Germany | 604/349 |
| 0366492 | 10/1906 | France | 604/349 |

OTHER PUBLICATIONS

Mox-C/S Conductive Rubber for EMI/RFI Shielding, Moxness, Products, Inc. (Compounds MS-60E02, MS-65E07, MS-70E03, MS-75E01, MS-75E03), Article Form Consumer Report, Mar. 1989, entitle "Can You Rely on Condoms?".

Primary Examiner—Robert A. Hafer
Assistant Examiner—Michael Brown
Attorney, Agent, or Firm—Frishauf, Holtz, Goodman & Woodward

[57] ABSTRACT

An electrically conductive condom includes a generally cylindrical protective sheath having an open end for receiving a penis therein and an opposite closed end, the sheath being made from a thin, elastic, electrically conductive material which may be formed from a non-conductive elastic material having electrically conductive particles embedded therein. The electrically conductive material is preferably a thin elastomeric material with small conductive particles, such as carbon and/or wsilver particles, embedded therein. A reinforcing layer may be secured to the open end of the sheath. Optionally, a retaining strap may be secured to the reinformcing layer for retaining the sheath on a person, and quick release is provided for releasably securing the retaining strap about a person so as to releasably secure the sheath on the person.

34 Claims, 1 Drawing Sheet

CONDUCTIVE CONDOM

BACKGROUND OF THE INVENTION

This invention relates generally to condoms, and more particularly, is directed to an electrically conductive condom.

The use of condoms to prevent conception and venereal infection during coitus is well known Further, condoms have been found to be an effective barrier against the AIDS virus (HIV) and their use can therefore reduce the risk of cross-infection. Conventionally, condoms have been made from a thin, electrically non-conductive rubber, plastic (elastic), lamb skin, or like material. In some instances, the condoms are lubricated with a "jelly" type material which has a non-petroleum type base. In this regard, spermicidally lubricated condoms may possibly also provide added protection against diseases such as the AIDS virus.

It will be appreciated, however, that the inner vaginal walls and the outer surface of the penis have nerve endings thereat. During normal intercourse, the nerve endings are stimulated by friction, which is reduced when using a condom. Such nerve endings also have electrical activity associated therewith, whereby electrical conduction occurs between the vaginal and penile nerve endings. However, the use of a condom made of an electrically non-conductive material, blocks electrical conduction, thereby further lessening sensations during coitus.

OBJECTS OF THE INVENTION

It is an object of the present invention to provide a condom that overcomes the aforementioned problems with the prior art.

It is another object of the present invention to provide an electrically conductive condom that also prevents conception and disease during coitus.

It is another object of the present invention to provide such a condom made of an elastic non-porous material having an electrically conductive material therein.

The above and other objects, features and advantages of the present invention will become readily apparent from the following detailed description which is to be read in connection with the accompanying drawings.

SUMMARY OF THE INVENTION

In accordance with an aspect of the present invention, an electrically conductive condom includes a generally tubular protective sheath having an open end for receiving a penis therein and an opposite closed end, the sheath being made from a thin, elastic, electrically conductive material.

In accordance with another aspect of the present invention, an electrically conductive condom includes a generally tubular protective sheath having an open end for receiving a penis therein and an opposite closed end, the sheath being made from a thin elastic, electrically conductive material; a reinforcing layer secured to the open end of the sheath; retaining strap means secured to the reinforcing layer for retaining the sheath on a person; and quick release means for releasably securing the retaining strap means about a person so as to releasably secure the sheath on the person.

In accordance with still another aspect of the present invention, an electrically conductive condom includes a generally tubular protective sheath having an open end for receiving a penis therein and an opposite closed end, the sheath being made from a thin, elastic, electrically conductive material; a splash guard secured to the open end of the sheath; retaining strap means secured to the splash guard for retaining the sheath on a person; and quick release means for releasably securing the retaining strap means a person so as to releasably secure the sheath on the person.

In any or all of the above embodiments, the electrically conductive material may be formed from a non-conductive elastic material having electrically conductive particles embedded therein.

DETAILED DESCRIPTION

Figure 1:
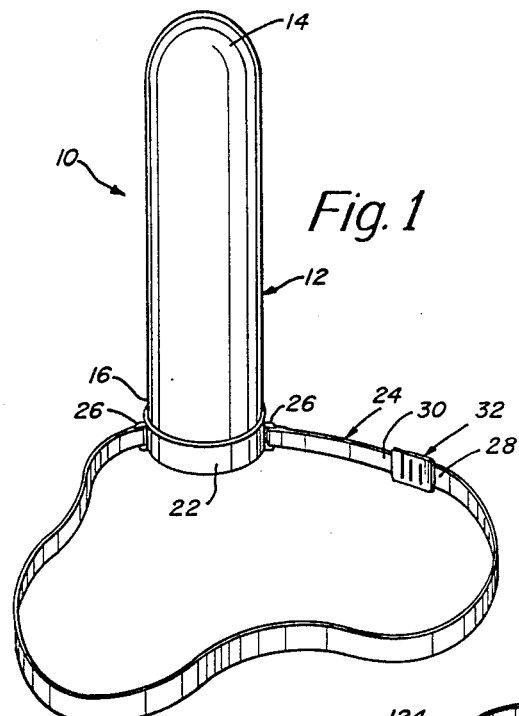
FIG. 1 is a perspective view of a male conductive condom according to one embodiment of the present invention.
Figure 3:
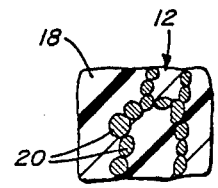
FIG. 3 is an enlarged cross-sectional view of a portion of the condoms of FIGS. 1 and 2.

Referring to the drawings in detail, and initially to FIG. 1 thereof, a male conductive condom 10 for insertion over a penis prior to penetration, includes a thin, protective, elastic sheath 12 of a generally cylindrical or tubular configuration and having a rounded closed end 14. The opposite end 16 of sheath 12 is open for insertion of the penis therethrough. According to the invention, sheath 12 is electrically conductive. This may be accomplished by making sheath 12 from an elastic insulating material 18, such as latex, urethane, rubber or the like, as is conventional, but also having microscopic conductive particles 20 embedded therein, as shown in the enlarged view in FIG. 3. For example, the material of sheath 12 can be an electroconductive polymer-latex composite as disclosed in U.S. Pat. No. 4,678,601 to Ham et al, a conductive rubber material as disclosed in U.S. Pat. No. 4,765,930 to Mashimo et al, or an electrically conductive silicone rubber sold by Moxness Products, Inc. of Racine, Wis. under the compound designations MS-60E02, MS-65E07 MS-70E03, MS-75E01 and MS75E03, the contents of all of which are incorporated herein by reference. In the Mashimo et al patent, the material is an electrically insulating rubber material containing conductive carbon black, while in the Moxness products, silicone is used as the elastomer binder with carbon as the conductive filler. A conductive sheath 12 may alternatively be a thin elastomeric material, such as latex, urethane, rubber or the like, in which is embedded a multitude of small silver particles (preferably spherical) of diameters (or sizes) smaller than the thickness of the elastic condom material, and preferably much smaller than said thickness. Silver and carbon particles may both be embedded in an elastomeric material to make it conductive. Other conductive particles could also be used alone or in combination.

Another type of material which is useful for embedding in the elastic material of the condom to make same conductive is silver-plated glass particles or beads, or silver-plated copper particles or beads. Such materials are preferably made with a very small particle size, for example substantially thinner than the thickness of the elastic condom material, which is generally about 0.002 inches thick. The particles can be, for example, about one micron in diameter, and can be regular or irregular microspheres or other shaped particles Also, the particles should have many contacts per square inch so as to provide better conductivity of the resulting condom. About one million contacts per square inch is achievable.

Carbon has a volume resistivity of about 2.5, silver-plated glass particles has a volume resistivity of about 0.010, and silver-plated copper particles has a volume resistivity of about 0.004, which is better than the two previously mentioned materials. As mentioned above, the particles discussed herein can be used singly or in any combination, to provide the desired overall conductivity of the resulting condom.

Figure 4:
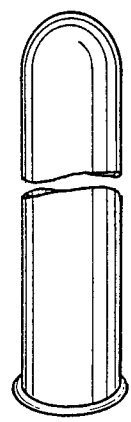
FIG. 4 is a perspective view of a conventional condom to which the present invention may be applied.
Figure 5:
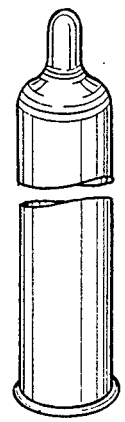
FIG. 5 shows a conventional condom with a sperm retaining pocket or well at the tip end thereof, to which the present invention may also be applied.

As shown in FIG. 1, open end 16 of sheath 12 has a reinforcing layer 22 thereabout. Reinforcing layer 22 can, for example, be made from a flat elastic material such as a heavy gauge latex laminated at open end 16. Alternatively, reinforcing layer 22 can be comprised of multiple folded layers of material 18 at open end 16. The condom may also take a more conventional form as shown, for example, in FIGS. 4 and 5.

An elastic retaining strap 24 has opposite ends thereof secured to reinforcing layer 22, preferably at diametrically opposite positions thereon. Securement of retaining strap 24 on reinforcing layer 22 can be effected by any suitable means, such as an adhesive. Alternatively, handles 26 of the same material as reinforcing layer 22 can be formed on reinforcing layer 22, and the opposite ends of retaining strap 24 can be secured thereto. As another alternative, retaining strap 24 can merely be slid or threaded through handles 26. Retaining strap 24 straps about the buttocks of the male in order to retain sheath 12 on the penis when the erection is lost. This helps prevent inadvertent removal of the condom and helps prevent body fluids from being interchanged or contacting the other person.

Retaining strap 24 is formed with free ends 28 and 30. A conventional quick release buckle 32 is associated with free ends 28 and 30 to releasably secure the same together and to provide for adjustment of the length of retaining strap 24.

With the above-described male conductive condom 10, because of microscopic conductive particles 20 in thin, elastic sheath 12, electrical conduction between the vaginal and penile nerve endings is enhanced, whereby sensations during coitus are increased.

Figure 2:
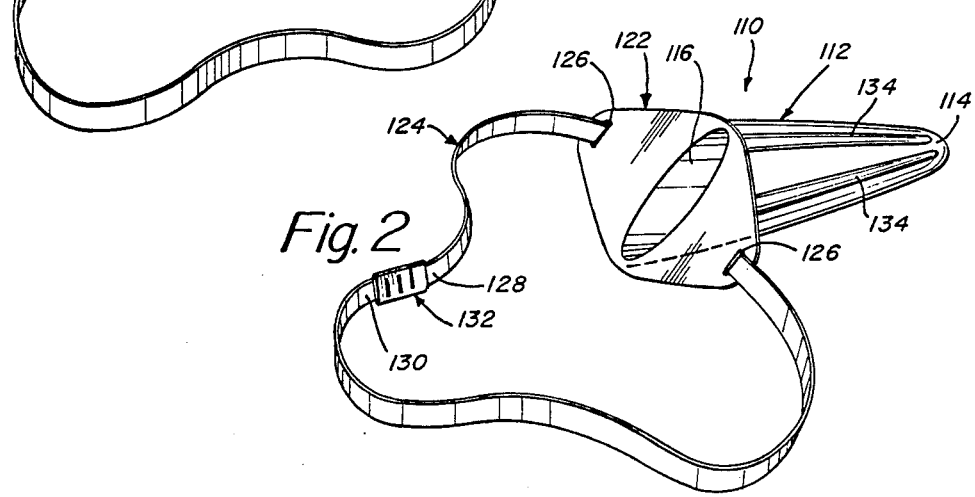
FIG. 2 is a perspective view of a female conductive condom according to another embodiment of the present invention.

Referring now to FIG. 2, a female conductive condom 110 according to another embodiment of the present invention will now be described, in which elements corresponding to those described above with respect to male conductive condom 10 are identified by the same reference numerals augmented by 100, and a detailed description of such common elements will be omitted herein for the sake of brevity.

Unlike male conductive condom 10, female conductive condom 110 is first placed in the vaginal cavity prior to insertion of the penis. In order to prevent withdrawal of sheath 112 during intercourse and to add some rigidity to sheath 112, tapered ribs 134 are formed on the external surface along the length of sheath 112. Accordingly, sheath 12 remains in the vaginal cavity during coitus. It will be appreciated that sheath 112 is preferably made from the same electrically conductive materials as sheath 12.

In place of reinforcing layer 22, female conductive condom 110 is formed with a splash guard 122 at open end 116 thereof. Splash guard 122 is also preferably made of the same conductive material as sheath 112.

Retaining strap 124 is formed with two free ends 128 and 130, and it is preferably identical to retaining strap 112. A quick release buckle 132, is associated with the two free ends 128 and 130. However, splash guard 122 is provided with two slits 126 used to secure retaining strap 124 thereto. It will further be appreciated that, in the case of female conductive condom 110, retaining strap 124 can also be used for removing sheath 112 from the vaginal cavity.

Thus, as with male conductive condom 10, female conductive condom 110 provides electrical conduction between the vaginal and penile nerve endings, whereby sensations during coitus are enhanced.

In order to further aid in the electrical conduction when using condoms 10 and 110, an internal grade of conductive gel or lubricant and/or a conductive gel spermicide can be used therewith. Such conductive gels are known for other purposes, for example, for use with electrodes for electro-cardiogram and transcutaneous electronic nerve stimulation (TENS) devices, and can be used with the present invention. The conductive gel would be applied to one or both condoms 10, 110 before penetration, and could be applied externally and/or internally of the condoms to improve electrical conduction and to also provide lubrication.

Having described specific preferred embodiments of the invention with reference to the accompanying drawings, it will be appreciated that the present invention is not limited to those precise embodiments and that various changes and modifications can be effected therein by one of ordinary skill in the art without departing from the spirit or scope of the invention, as defined in the appended claims.

I claim:

1. An electrically conductive condom comprising a thin, protective sheath having an open end for receiving a penis therein and an opposite closed end, said sheath being made from an elastic material including electrically conductive means for rendering the elastic material electrically conductive, for increasing sensitivity with respect to adjacent nerve endings of a human body.

2. An electrically conductive condom according to claim 1, wherein said elastic material includes a non-conductive elastic material, and said electrically conductive means includes electrically conductive particles embedded in said non-conductive elastic material.

3. An electrically conductive condom according to claim 2, wherein said non-conductive elastic material is selected from the group consisting of latex, rubber and urethane.

4. An electrically conductive condom according to claim 2, wherein said electrically conductive particles are of a microscopic size.

5. An electrically conductive condom according to claim 2, wherein said electrically conductive particles are made from carbon.

6. An electrically conductive condom according to claim 2, wherein said electrically conductive particles are made from silver.

7. An electrically conductive condom according to claim 6, wherein said silver particles are substantially spherical and have diameters substantially less than the thickness of said elastic sheath material.

8. An electrically conductive condom according to claim 1, wherein said open end of said sheath has a reinforcing layer secured thereto.

9. An electrically conductive condom according to claim 8, wherein said reinforcing layer is made from a plurality of folded layers of said sheath at said open end thereof.

10. An electrically conductive condom according to claim 8, further including retaining strap means secured to said reinforcing layer for retaining said sheath on a person.

11. An electrically conductive condom according to claim 1, further including retaining strap means coupled to said sheath for retaining said sheath on a person.

12. An electrically conductive condom according to claim 11, wherein said retaining strap means includes quick release means for releasably securing said sheath on the person.

13. An electrically conductive condom according to claim 1, wherein said sheath has a substantially cylindrical or tubular configuration.

14. An electrically conductive condom according to claim 1, wherein said sheath includes a plurality of rib means extending along the length of an outer surface thereof for retaining said sheath in a vaginal cavity.

15. An electrically conductive condom according to claim 14, wherein each of said rib means has a tapering configuration.

16. An electrically conductive condom according to claim 1, further including splash guard means secured to the open end of said sheath for providing protection against contact by liquids.

17. An electrically conductive condom according to claim 16, further including retaining strap means secured to said splash guard means for retaining said sheath on a person.

18. An electrically conductive condom according to claim 1, further including conductive gel means on at least one surface said sheath for increasing electrical conduction thereof.

19. An electrically conductive condom according to claim 1, wherein said elastic material is selected from the group consisting of latex, rubber and urethane.

20. An electrically conductive condom comprising: a thin, generally tubular protective sheath having an open end for receiving a penis therein and an opposite closed end, said sheath being made from an elastic, electrically conductive material formed from a non-conductive elastic material having electrically conductive particles embedded therein for increasing sensitivity with respect to adjacent nerve endings of a human body;
reinforcing means at said open end of said sheath for strengthening said open end of said sheath; and
retaining strap means secured to said reinforcing layer for retaining said sheath on a person.

21. An electrically conductive condom according to claim 20, wherein said retaining strap means comprises quick release means for releasably securing said retaining strap means about a person so as to releasably secure said sheath on the person.

22. An electrically conductive condom according to claim 20, wherein said non-conductive elastic material is selected from the group consisting of latex, rubber and urethane.

23. An electrically conductive condom according to claim 20, wherein said electrically conductive particles are of a microscopic size.

24. An electrically conductive condom according to claim 20, wherein said electrically conductive particles are made from carbon.

25. An electrically conductive condom according to claim 20, wherein said electrically conductive particles are made from silver.

26. An electrically conductive condom according to claim 25, wherein said silver particles are substantially spherical and have diameters substantially less than the thickness of said elastic sheath material.

27. An electrically conductive condom comprising:
a thin, generally tubular protective sheath having an open end for receiving a penis therein and an opposite closed end, said sheath being made from an elastic, electrically conductive material formed from a non-conductive elastic material having electrically conductive particles embedded therein for increasing sensitivity with respect to adjacent nerve endings of a human body;
a splash guard secured to said open end of said sheath; and
retaining strap means secured to said splash guard for retaining said sheath on a person.

28. An electrically conductive condom according to claim 27, wherein said retaining strap means comprises quick release means for releasably securing said retaining strap means a person so as to releasably secure said sheath on the person.

29. An electrically conductive condom according to claim 27, wherein said non-conductive elastic material is selected from the group consisting of latex, rubber and urethane.

30. An electrically conductive condom according to claim 27, wherein said electrically conductive particles are of a microscopic size.

31. An electrically conductive condom according to claim 27, wherein said electrically conductive particles are made from carbon.

32. An electrically conductive condom according to claim 27, wherein said electrically conductive particles are made from silver.

33. An electrically conductive condom according to claim 32, wherein said silver particles are substantially spherical and have diameters substantially less than the thickness of said elastic sheath.

34. An electrically conductive condom according to claim 27, wherein said sheath includes a plurality of rib means extending along the length of an outer surface thereof for retaining said sheath in a vaginal cavity.

* * * * *